US00PP28318P3

(12) United States Plant Patent
Yencho et al.

(10) Patent No.: US PP28,318 P3
(45) Date of Patent: Aug. 22, 2017

(54) SWEETPOTATO PLANT NAMED 'NCORNSP-019SCSHLM'

(50) Latin Name: ***Ipomoea batatas* (L.) Lam.**
Varietal Denomination: NCORNSP-019SCSHLM

(71) Applicant: North Carolina State University, Raleigh, NC (US)

(72) Inventors: George Craig Yencho, Raleigh, NC (US); Meri K. Reeber, Apex, NC (US); Kenneth Vincent Pecota, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 20 days.

(21) Appl. No.: 14/756,939

(22) Filed: Oct. 30, 2015

(65) Prior Publication Data

US 2016/0316604 P1 Oct. 27, 2016

(30) Foreign Application Priority Data

Apr. 24, 2015 (CA) ..... 15-8652

(51) Int. Cl.
*A01H 5/12* (2006.01)

(52) U.S. Cl.
USPC ..... Plt./258

(58) Field of Classification Search
USPC ..... Plt./258, 373
See application file for complete search history.

*Primary Examiner* — Susan McCormick Ewoldt
(74) *Attorney, Agent, or Firm* — Myers Bigel, P.A.

(57) ABSTRACT

'NCORNSP-019SCSHLM' is a moderately-compact to compact, non-twining, upright variety producing many short shoots. It is distinguishable from other cultivars by its yellow green heart shaped leaves that are entire with a cordate base; a compact habit and semi-erect mounding plant architecture. The lime green leaves of this plant, short internodes, and the plant architecture are what makes 'NCORNSP-019SCSHLM' unique amongst the current ornamental sweetpotatoes in the marketplace. 'NCORNSP-019SCSHLM' also exhibits very good vigor and is very well branched. In greenhouse and field trials, 'NCORNSP-019SCSHLM' has been shown to be much less vigorous than *Ipomoea batatas* 'Margarita' and 'Blackie' and is suitable for use as a landscape or containerized plant. The production of flowers by 'NCORNSP-019SCSHLM' is sporadic under short day conditions.

3 Drawing Sheets

Latin name of the genus and species: The Latin name of the novel plant variety disclosed herein is *Ipomoea batatas* (L.) Lam.

Varietal denomination: The inventive variety of *Ipomoea batatas* (L.) Lam. disclosed herein has been given the varietal denomination 'NCORNSP-019SCSHLM.'

RELATED APPLICATION INFORMATION

This application claims priority to Canadian Plant Breeders Rights Application No. 15-8652, filed Apr. 24, 2015; the disclosure of which is incorporated herein by reference in its entirety.

BACKGROUND OF THE INVENTION

*Ipomoea batatas* is a member of the morning glory family Convolvulaceae. This species is grown worldwide and it exhibits a wide range of plant forms and colors. The cultivated members of *Ipomoea batatas* grown by farmers worldwide are commonly produced for consumption of their nutritious, enlarged storage roots. These types typically produce a fast growing green vine that has a wide variety of leaf shapes ranging from palmate and deeply lobed, to cordate or triangular shaped leaves with no lobes.

Like their edible forms, *Ipomoea batatas* ornamental sweetpotato plants are a heat-loving, drought-tolerant, perennial vine typically grown as an annual. However, ornamental sweetpotato plants are distinguished from the edible cultivated forms in that they possess unique foliage colors, leaf shapes, and growth habits, which have significant value in the ornamental marketplace.

Ornamental sweetpotatoes are desirable in the landscape and ornamental industries because their foliage comes in a wide variety of colors (e.g. pale yellow to dark purple with some exhibiting temporal and individual leaf color variegation patterns) and plant shapes (e.g. mounded and very compact to prostrate and highly spreading). They can be grown in a potted plant and/or mixed planting format, and they have the ability to cover a large space or hang over walls and decorative pots creating brightly colored and textured backdrops in gardens and patios. Most ornamental sweetpotatoes grow and last the entire growing season and they require little maintenance. Moreover, these plants have few insect or disease problems.

To meet the growing horticultural demand for ornamental sweetpotatoes, it is desirable to produce new cultivars of ornamental sweetpotato with new or improved foliage colors, variegation patterns, leaf shapes, and plant architectures. In addition, it would be advantageous to develop cultivars of ornamental sweetpotato exhibiting a more compact growth that do not out-compete other species in mixed containers.

'NCORNSP-019SCSHLM' was bred to meet the increasing demand for new ornamental sweetpotatoes and this plant patent application describes this new and distinct invention. 'NCORNSP-019SCSHLM' is a moderately-compact to compact, non-twining, upright variety producing many short shoots. It is distinguishable from other cultivars by its yellow green heart shaped leaves that are entire with a cordate base, a compact habit and semi-erect mounding plant architecture. The lime green leaves of this plant, short internodes, and the plant architecture are what makes 'NCORNSP-019SCSHLM' unique amongst the current ornamental sweetpotatoes in the marketplace, 'NCORNSP-019SCSHLM' also exhibits very good vigor and is very well branched. In greenhouse and field trials conducted since 2010 by the breeding program and industry collaborators 'NCORNSP-019SCSHLM' has been shown to be much less vigorous than *Ipomoea batatas* 'Margarita' and 'Blackie' and is suitable for use as a landscape or containerized plant. The production of flowers by 'NCORNSP-019SCSHLM' is sporadic under short day conditions.

Lineage. 'NCORNSP-019SCSHLM' (breeding designation NC7051-040ORN) originated from a conventional cross between the proprietary *Ipomoea batatas* breeding lines NC5973-009ORN (female parent; not patented) and NC6749-006ORN (male parent; not patented). Botanical seed was harvested from this and other ornamental sweetpotato lines planted in our winter greenhouse-crossing block between September of 2009 and March of 2010 in Raleigh, N.C. NC5973-009ORN resulted from a conventional cross between the proprietary *Ipomoea batatas* breeding lines 'NC2749-013ORN' (female parent; not patented) and NC4508-003ORN (male parent; not patented). NC6749-006ORN resulted from a conventional cross between the proprietary *Ipomoea batatas* breeding lines NC4748-001ONR (female parent; not patented) and 'Sweet Caroline Sweetheart Red' (male parent; U.S. Plant Pat. No. 19,013, Jul. 15, 2008) Botanical seed from this family were planted in the greenhouses in Spring 2010. The first cycle of selection on the population was exercised in the seedling trays and survivors were transferred to a single 6-inch pot, which was then maintained in the greenhouse. Cuttings (2 each) were taken from the plants in May 2010 and planted in the field as 2-plant unreplicated plots during mid June 2010. The single, individual plant now known as 'NCORNSP-019SCSHLM' was selected Aug. 11, 2010 because of its combination of exceptional features, and has been propagated asexually in Raleigh, N.C. since that time.

Asexual Reproduction. Since its selection, *Ipomoea batatas* 'NCORNSP-019SCSHLM' has been asexually reproduced in North Carolina predominantly by vegetative propagation of vine cuttings. Successively, there have been five cycles of vegetative propagation, one cycle of tissue culture micropropagation, and multiple vegetative propagation cycles to increase the plant population. Asexual reproduction of 'NCORNSP-019SCSHLM' by cuttings has shown that the unique features of the new cultivar are stable and the plant reproduces true to type in successive generations.

SUMMARY OF THE INVENTION

'NCORNSP-019SCSHLM' is a moderately-compact to compact, non-twining, upright variety producing many short shoots. It is distinguishable from other cultivars by its yellow green heart shaped leaves that are entire with a cordate base, a compact habit and semi-erect mounding plant architecture. The lime green leaves of this plant, short internodes, and the plant architecture are what makes 'NCORNSP-019SCSHLM' unique amongst the current ornamental sweetpotatoes in the marketplace. 'NCORNSP-019SCSHLM' also exhibits very good vigor and is very well branched. In greenhouse and field trials conducted since 2010 by the breeding program and industry collaborators, 'NCORNSP-019SCSHLM' has been shown to be much less vigorous than *Ipomoea batatas* 'Margarita' and 'Blackie' and is suitable for use as a landscape or containerized plant. The production of flowers by 'NCORNSP-019SCSHLM' is sporadic under short day conditions.

DESCRIPTION OF THE PHOTOGRAPHS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatassis*.

The photographs for FIG. 1 and FIG. 3 were taken in Raleigh, N.C. on Oct. 14, 2014.

The photograph for FIG. 2 was taken in Clinton, N.C. on Jul. 14, 2014.

DETAILED BOTANICAL DESCRIPTION

The following is a detailed description of the botanical characteristics of a new and distinct cultivar of *Ipomoea batatas* plant known by the cultivar name *Ipomoea batatas* 'NCORNSP-019SCSHLM'. All colors cited herein refer to The Royal Horticultural Society Colour Chart designations (The Royal Horticultural Society, London, 2007, $5^{th}$ ed. except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetic Resources (IBPGR), Rome, Italy (CIP, AVRDC, IBPGR. 1991. Descriptors for Sweet Potato. Huaman, Z., editor. International Board for Plant Genetic Resources, Rome, Italy, 134pp.). Where dimensions, sizes, colors, and other characteristics are given, it is to be understood that such characteristics are approximations or averages set forth as accurately as practicable.

Figure 1:
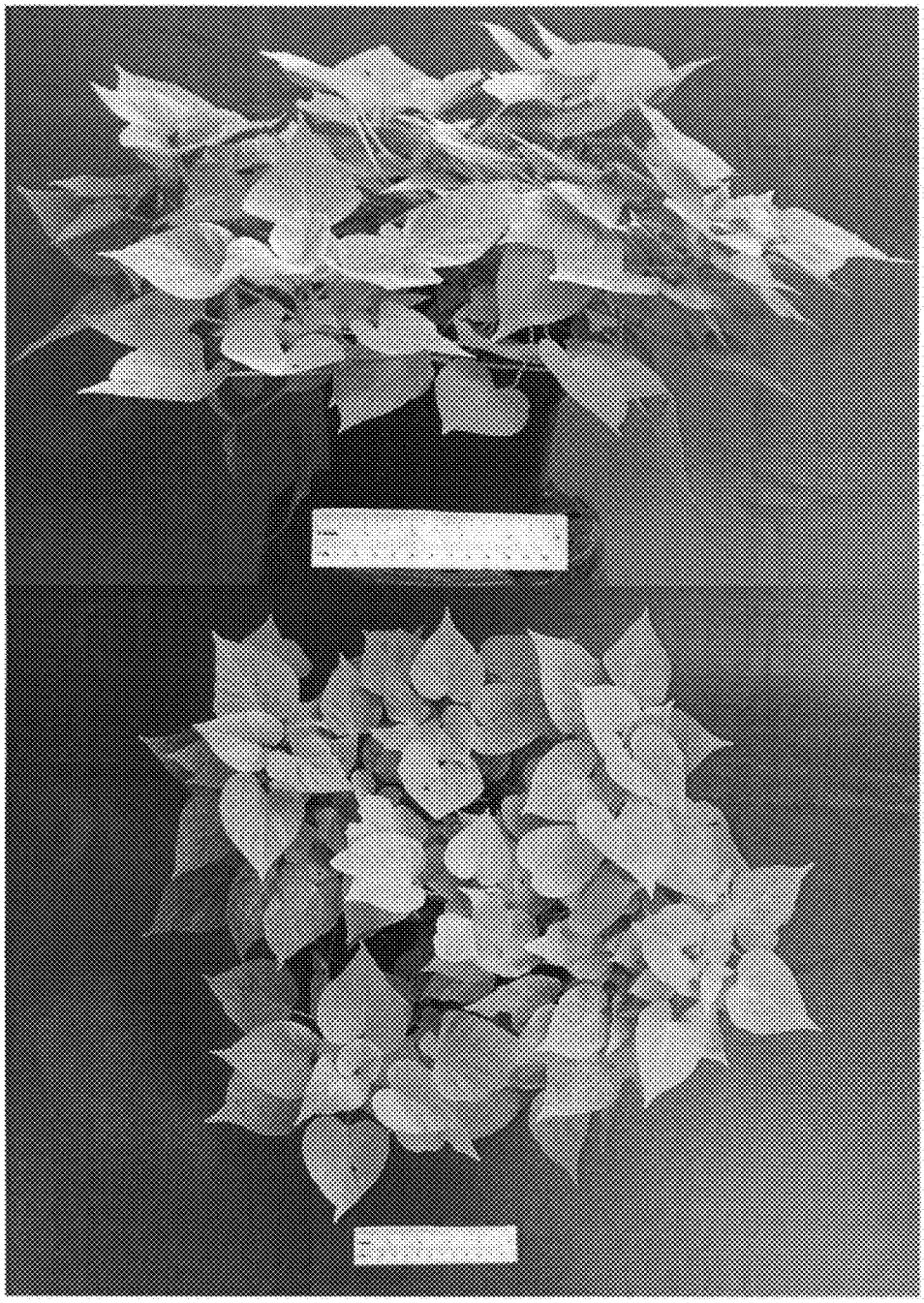
FIG. 1 is a color photograph of a typical specimen of greenhouse grown *Ipomoea batatas* 'NCORNSP-019SCSHLM' in a 6-inch pot from the side and top, 53 days after planting.

The descriptions reported herein are from 53-day-old specimens grown individually in six-inch azalea pots (FIG. 1). The plants were grown in Raleigh, N.C., under commercial practice in a glass-covered greenhouse, where, during the fall, day and night temperatures range between 25-40° C. and 22-26° C., respectively. After rooting, plants were treated with 200 ppm 20-10-20 fertilizer daily. Plant histories were taken during the second week of October 2014 in Raleigh, N.C. 'NCORNSP-019SCSHLM' has not been observed under all possible environmental conditions; therefore, the phenotype may vary with variations in the environment such as season, temperature, light intensity, day length, cultural conditions, and the like.

Botanical classification:

*Botanical name.*—*Ipomoea batatas* (L.) Lam.

*Common name.*—Ornamental Sweetpotato.

*Variety name.*—'NCORNSP-019SCSHLM'.

*Growth conditions.*—*Ipomoea batatas* 'NCORNSP-019SCSHLM' has very good vigor, a moderate growth rate, and is very adaptable to container culture. In locales with mild winter conditions, *Ipomoea batatas* 'NCORNSP-019SCSHLM' will grow perennially; otherwise it is an annual plant. Similar to cultivated sweetpotatoes, wind or rain rarely causes much damage to 'NCORNSP-019SCSHLM', but if damage does occur, the plant drops the damaged leaves and grows new shoots at nodes where the leaves were lost. Under low light levels in a greenhouse, 'NCORNSP-019SCSHLM' can develop intumescence, which will remain on the affected foliage, but will be outgrown with new foliage.

Branches:

*Branching habitat.*—Freely-branching with about 4-5 primary lateral branches coming off the stem. Very dense foliage and no pinching is required to stimulate branching. Branch texture is glabrous.

*Vegetative lateral branching.*—Length: about 22.1 cm. Diameter: about 0.5 cm. Internodes are very short with an average length of about 0.7 cm.

*Secondary lateral shoots.*—The number of secondary lateral shoots varies, but averages about 4 with several short additional shoots. Length: about 11 cm. Diameter: about 0.4 cm.

*Stem.*—Round and smooth with an upward, outward and slightly undulating aspect and very strong, slightly flexible strength. Color: Yellow Green (between RHS 145A and 144D).

*Adventitious roots.*—Present at nodes. Color: Yellow Green (between RHS 145A and 144D) with Brown (RHS 199A).

*Petiole.*—Petioles are held upward and splay the leaf slightly vertical. Leaf petiole has a smooth texture with a matte finish. Length: about 8.2 cm. Diameter: about 0.3 cm. Color: Yellow Green (between RHS 145A and 144B) with Brown (RHS 200B-200C) on young leaves at apical meristem.

Figure 2:
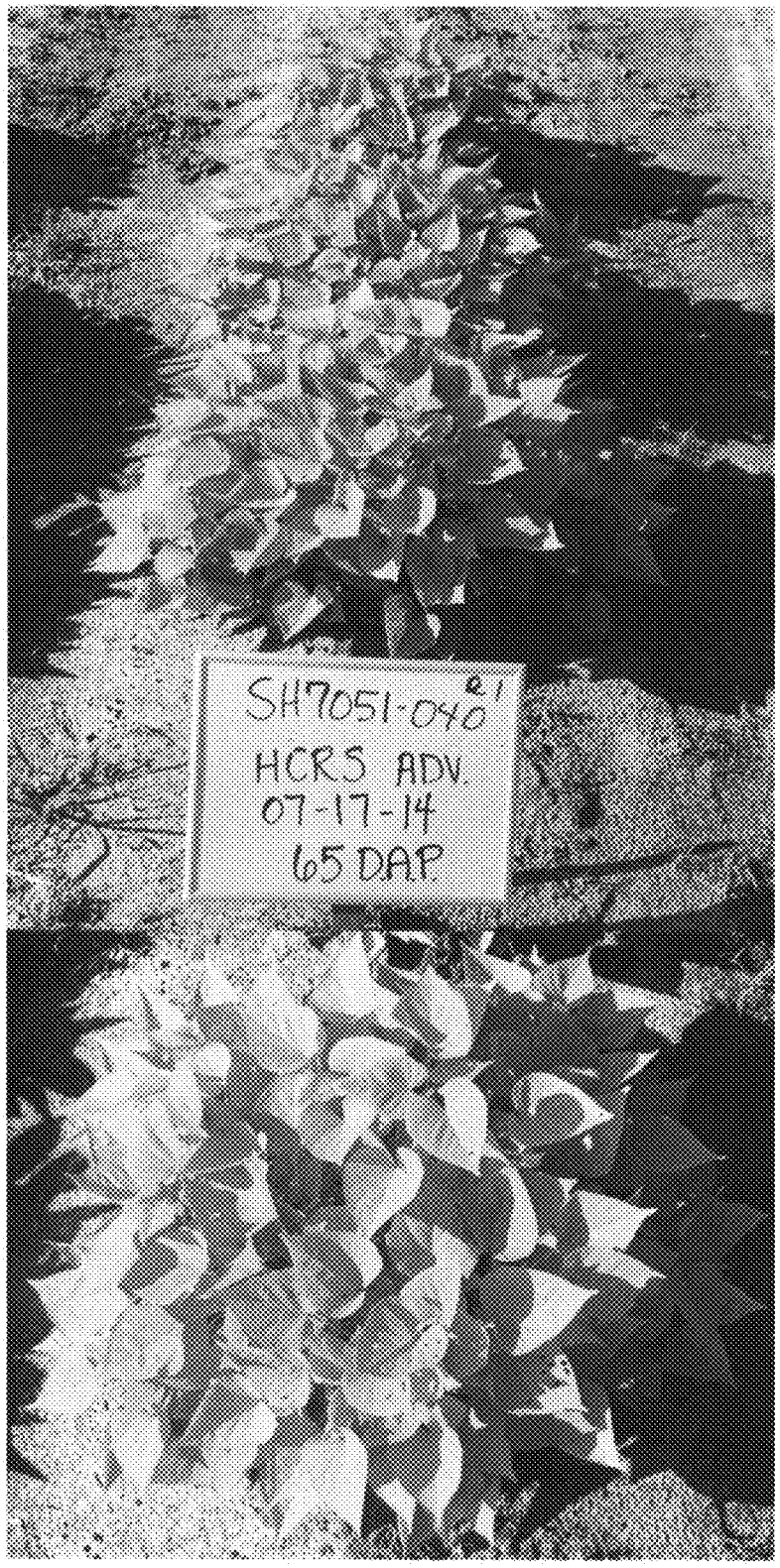
FIG. 2 is a color photograph of a typical specimen of *Ipomoea batatas* 'NCORNSP-019SCSHLM' from side and top in the field, 65 days after planting.
Figure 3:
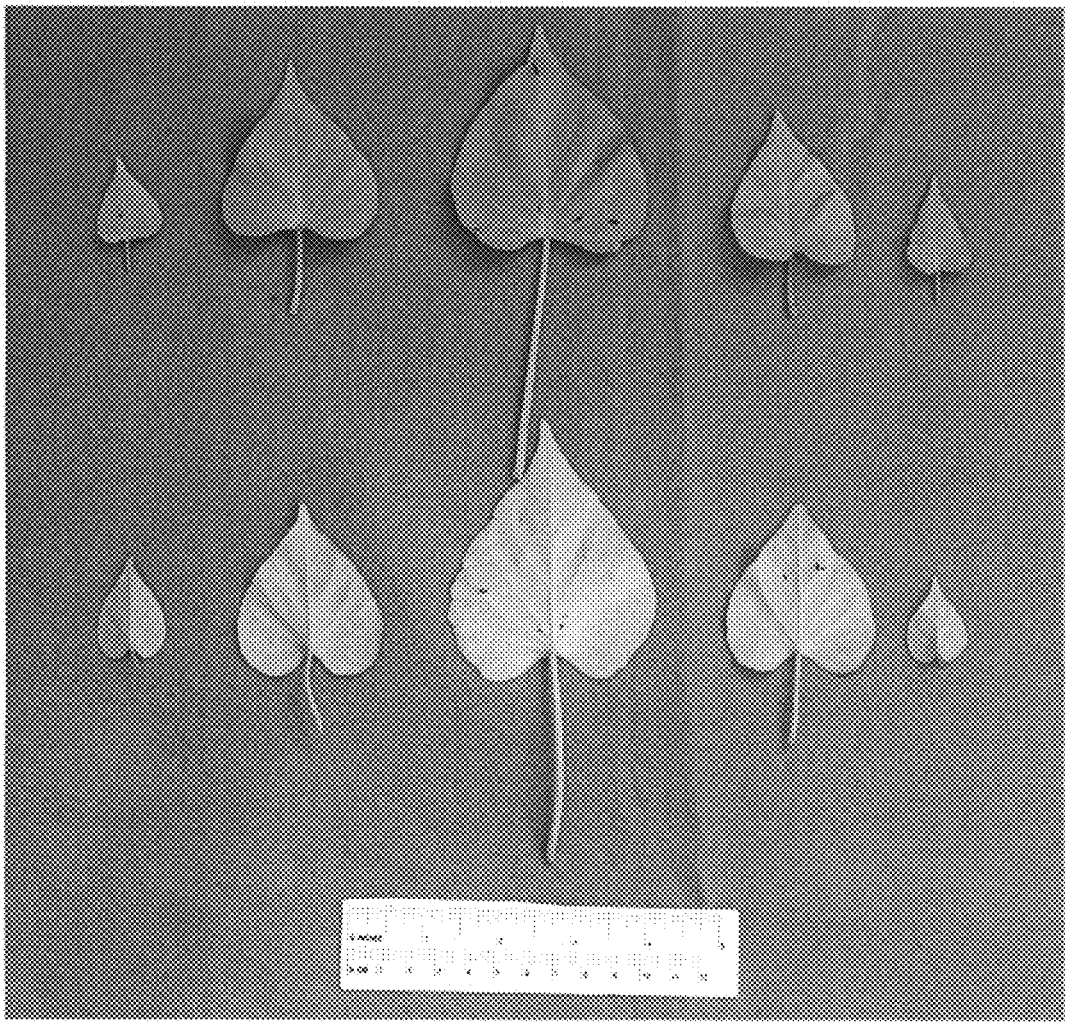
FIG. 3 is a color photograph showing the variety of leaves produced by *Ipomoea batatas* 'NCORNSP-019SCSHLM' and the lower surface of the leaf (bottom row), 53 days after planting.

Foliage: Leaves are alternate and tend to slightly spiral around the stem. They are simple and cordate to slightly deltoid with an entire margin. Leaves have no lobing. Leaf shape is somewhat variable as is size (see FIG. 2). Leaf texture is smooth with a matte finish on both the upper and lower surface.

*Quantity.*—Moderately-heavily foliated, with about 16 leaves per lateral branch.

*Mature leaf length.*—About 9.3 cm.

*Mature leaf width.*—About 7.1 cm.

*Leaf margin.*—Entire.

*Leaf apex.*—Acute.

*Leaf base.*—Cordate to slightly Deltoid.

*Leaf texture.*—Glabrous texture and matte finish.

*Venation.*—Cross-venulate. Texture: glabrous.

*Color.*—Leaves are yellow green and range within that palate as they mature. See Table 1.

TABLE 1

| Leaf description | | |
|---|---|---|
| Leaf Structure | Upper Surface | Lower Surface |
| Young Leaf | Yellow Green (RHS144A-B) | Greyed Yellow Green (RHS 147D) |
| Mature Leaf | Yellow Green (between and amongst RHS 144A and 144B and 144C) | Yellow Green (between and amongst RHS 145A and 144B and 144C) |
| Vein-mature leaf | Yellow Green (RHS144A-B) | Yellow Green to Greyed Yellow Green (between and amongst RHS144C and 147D) |
| Vein-young leaf | Yellow Green (RHS144A-B) | Green (between and amongst RHS 145A and 144B and 144C) with Brown at petiole junction (RHS200B-C) |

Inflorescence: *Ipomoea batatas* 'NCORNSP-019SCSHLM' flowers sporadically throughout the season in response to a variety of stressful conditions (e.g., drought, nutrient stress, cloudy weather). Shorter day length enhances flowering, but the precise photoperiod for flower induction is currently unknown. Solitary, regular funnel-form flowers arising, from leaf axils on secondary lateral branches are formed. Peduncles are yellow green (between and amongst RHS 145A and 144B and 144 C) with a smooth texture. Peduncle length: about 1.7 cm, peduncle width: about 0.3 cm. Flower buds are pale green-yellow fading to purple at the tip and lanceolate to elliptic (RHS 144C-D fading to 27B, 76B at tip). Flower bud length: about 1.5 cm, flower bud width: about 0.5 cm. Corolla width: about 4.2 cm, corolla length: about 3.4 cm. Limb color: Cream to light lavender (between RHS 69D and 76D) on both inner and outer surface. The inner throat color gets lighter from base to limb going from purple (between RHS N80N and N81A) at the base to lavender (76A) near the limb. The limb is pentagonal with slight fragrance. The two outer sepals are shorter than the inner sepals. Average sepal length: 0.8 cm, average sepal width: 0.4 cm. The sepals are obovate with an obtuse to caudate apex and light green to green (RHS 145C-D with 145A) in color. Sepal texture is glabrous on both the upper and lower surface. A single pistil consists of one style and one stigma about 2.1 cm in length. Stigma and style are both cream (RHS 155A-B). The stigma is exerted relative to the stamens. The flower averages five cream-light lavender stamens. Each stamen consists of a single cream-light lavender filament averaging 1.4 cm in length topped with a single cream-white anther averaging 0.3 cm in length. Filament color: cream-light lavender (RHS N155A-B, 76B). Anther color: cream (RHS 158D, 155A-B). Pollen color: cream (RHS 158D, 155A-B). Pollen is sparse. To date, fruit has not been observed under normal greenhouse conditions.

Storage root coloration: *Ipomoea batatas* 'NCORNSP-019SCSHLM' plants form no, to very small, underground storage roots that are occasionally malformed and do not meet USDA Sweetpotato Storage Root Grade Standards. Fibrous roots typically posses cream (RHS 155D) with pink (RHS186B-C). Storage roots that are formed possess red purple skin (RHS71A, N77B) with yellow-white striations (RHS 158C-D). Flesh color is greyed orange-yellow (RHS 163D, 162B-C) with hints of purple-greyed purple (RHS N77B, 186A-B).

COMPARISON WITH OTHER *IPOMOEA BATATAS* CULTIVARS

'NCORNSP-019SCSHLM' is very distinct based on leaf shape and plant architecture. Of the common cultivars of ornamental sweetpotato, 'NCORNSP-019SCSHLM' is best compared with the 'Sweet Caroline Sweetheart Light Green' (U.S. Plant Pat. No. 18,572) and 'IPOSGLGRE' (U.S. Plant Pat. No. 22,279) cultivars (Table 2). Like 'Sweet Caroline Sweetheart Light Green' and 'Sweet Georgia Heart Light Green', 'NCORNSP-019SCSHLM' has yellow green leaves. However, the leaves of 'NCORNSP-019SCSHLM' are entire with a cordate-deltoid base compared to those of 'Sweet Caroline Sweetheart Light Green', which are entire with a cordate base, and those of 'Sweet Georgia Heart Light Green', which have a cordate base, a slightly savoy texture, and slight, occasional toothing and lobing.

'NCORNSP-019SCSHLM' has a moderately-compact to compact, upright, non-twining plant habit compared with the twining to slightly trailing plant habit of 'Sweet Caroline Sweetheart Light Green'. Furthermore, 'NCORNSP-019SCSHLM' has a smaller average leaf size compared with the larger leaves of 'IPOSGLGRE' and shorter primary lateral branches than both 'Sweet Caroline Sweetheart Light Green' and 'IPOSGLGRE'. Unlike 'Sweet Carolina Sweetheart Light Green', which has thin, twining vines, 'NCORNSP-019SCSHLM' has thicker, stronger stems.

TABLE 2

Comparison of 'NCORNSP-019SCSHLM' with other *Ipomoea batatas* Cultivars

| Characteristic | 'NCORNSP-019SCSHLM' | 'Sweet Caroline Sweetheart Light Green; (U.S. Plant Pat. No. 18,572) | 'IPOSGLGRE' (U.S. Plant Pat. No. 22,279) |
|---|---|---|---|
| Plant Habit | Moderately Compact-Compact, Upright and Non-Twining | Twining, Slightly Trailing | Moderately Compact |
| Average Leaf Length and Width | Length: 9.3 cm Width: 7.1 cm | Length: 8.7 cm Width: 7.8 cm | Length: 11.5 cm Width: 9.7 cm |
| Average Primary Lateral Branch Length and Diameter | Length: 22.1 cm Diameter: 0.5 cm | Length: 48.7 cm Diameter: 0.2 cm | Length: 48.7 cm Diameter: 0.5 cm |
| Leaf Shape | Entire. Cordate with cordate-deltoid base | Entire. Cordate with cordate base | Occasional toothing-lobing. Slight savoy texture. Cordate with cordate base |

Disease or pest resistance: 'NCORNSP-019SCSHLM' is susceptible to whiteflies and thrips in a greenhouse environment. 'NCORNSP-019SCSHLM' is susceptible to Sweetpotato Feathery Mottle Virus and damage by Japanese beetles in a field environment. It's resistance or susceptibility to other known insects and pathogens of sweetpotato is unknown. Under low light conditions, slight edema may occur.

What is claimed is:

1. A new and distinct cultivar of *Ipomoea batatas* plant named 'NCORNSP-019SCSHLM', substantially as illustrated and described herein.

* * * * *